(12) United States Patent
Schumacher

(10) Patent No.: US 11,863,037 B2
(45) Date of Patent: *Jan. 2, 2024

(54) COMPRESSIBLE MOTOR, IMPLANTATION ARRANGEMENT, AND METHOD FOR POSITIONING THE MOTOR

(71) Applicant: ECP ENTWICKLUNGSGESELLSCHAFT MBH, Aachen (DE)

(72) Inventor: Joerg Schumacher, Aachen (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/576,096

(22) Filed: Jan. 14, 2022

(65) Prior Publication Data

US 2022/0211994 A1 Jul. 7, 2022

Related U.S. Application Data

(63) Continuation of application No. 16/436,000, filed on Jun. 10, 2019, now Pat. No. 11,253,692, which is a
(Continued)

(30) Foreign Application Priority Data

Oct. 11, 2013 (EP) .................... 13188380

(51) Int. Cl.
*A61M 60/40* (2021.01)
*H02K 3/47* (2006.01)
(Continued)

(52) U.S. Cl.
CPC .............. *H02K 3/47* (2013.01); *A61M 60/122* (2021.01); *A61M 60/216* (2021.01);
(Continued)

(58) Field of Classification Search
CPC .......... H02K 3/47; H02K 99/20; H02K 33/12; H02K 3/02; H02K 33/16; A61M 60/122;
(Continued)

(56) References Cited

U.S. PATENT DOCUMENTS

| 4,753,221 A | 6/1988 | Kensey et al. |
| 5,749,855 A | 5/1998 | Reitan |

(Continued)

FOREIGN PATENT DOCUMENTS

| CA | 3148909 A1 | 6/2010 |
| DE | 29921352 U1 | 4/2001 |

(Continued)

OTHER PUBLICATIONS

Office Action from corresponding Japanese Application No. 2021-030621 dated Nov. 1, 2022 (8 pp.).
(Continued)

*Primary Examiner* — Scott M. Getzow
(74) *Attorney, Agent, or Firm* — Botos Churchill IP Law LLP

(57) ABSTRACT

The invention relates to a motor with a stator and a rotor, which can be driven about an axial direction. The invention is characterized in that at least one of the stator and the rotor, in particular the stator, which has a winding arrangement that can be supplied with a current, can be radially compressed and expanded.

23 Claims, 9 Drawing Sheets

US 11,863,037 B2
Page 2

Related U.S. Application Data continuation of application No. 15/662,884, filed on Jul. 28, 2017, now Pat. No. 10,342,904, which is a continuation of application No. 15/028,588, filed as application No. PCT/EP2014/071705 on Oct. 9, 2014, now Pat. No. 9,750,860.

(51) Int. Cl.
| | |
|---|---|
| *H02K 99/00* | (2014.01) |
| *A61M 60/419* | (2021.01) |
| *A61M 60/422* | (2021.01) |
| *A61M 60/865* | (2021.01) |
| *A61M 60/825* | (2021.01) |
| *A61M 60/216* | (2021.01) |
| *A61M 60/122* | (2021.01) |
| *A61M 60/148* | (2021.01) |
| *A61M 60/414* | (2021.01) |

(52) U.S. Cl.
CPC ........ *A61M 60/419* (2021.01); *A61M 60/422* (2021.01); *A61M 60/825* (2021.01); *A61M 60/865* (2021.01); *H02K 99/20* (2016.11); *A61M 60/148* (2021.01); *A61M 60/414* (2021.01); *A61M 2205/0266* (2013.01); *A61M 2205/04* (2013.01)

(58) Field of Classification Search
CPC .............. A61M 60/216; A61M 60/419; A61M 60/422; A61M 60/825; A61M 60/865; A61M 60/148; A61M 60/414; A61M 2205/0266; A61M 2205/04; A61M 1/024; A61M 60/205
See application file for complete search history.

(56) References Cited

U.S. PATENT DOCUMENTS

| | | | |
|---|---|---|---|
| 5,964,694 | A | 10/1999 | Siess et al. |
| 6,018,208 | A | 1/2000 | Maher et al. |
| 6,368,075 | B1 | 4/2002 | Fremerey |
| 7,011,620 | B1 | 3/2006 | Siess |
| 7,393,181 | B2 | 7/2008 | McBride et al. |
| 2005/0147512 | A1 | 7/2005 | Chen et al. |
| 2009/0062597 | A1 | 3/2009 | Shifflette |
| 2010/0076247 | A1 | 3/2010 | Zilbershlag et al. |
| 2011/0275884 | A1 | 11/2011 | Scheckel |
| 2012/0041254 | A1 | 2/2012 | Scheckel |
| 2013/0041202 | A1 | 2/2013 | Toellner |
| 2013/0138205 | A1 | 5/2013 | Kushwaha et al. |
| 2013/0177409 | A1 | 7/2013 | Schumacher et al. |
| 2013/0204362 | A1 | 8/2013 | Toellner et al. |
| 2017/0356454 | A1 | 12/2017 | Scheckel |

FOREIGN PATENT DOCUMENTS

| | | | |
|---|---|---|---|
| EP | 2047873 | A1 | 4/2009 |
| EP | 2218469 | A1 | 8/2010 |
| EP | 2229965 | A1 | 9/2010 |
| EP | 2299119 | A1 | 3/2011 |
| EP | 2338540 | A1 | 6/2011 |
| EP | 2338541 | A1 | 6/2011 |
| EP | 2363157 | A1 | 9/2011 |
| EP | 2407185 | A1 | 1/2012 |
| EP | 2407186 | A1 | 1/2012 |
| EP | 2407187 | A1 | 1/2012 |
| JP | 2000511759 | A | 9/2000 |
| JP | 2000512191 | A | 9/2000 |
| JP | 2002535059 | A | 10/2002 |
| JP | 2015503940 | A | 2/2015 |
| JP | 2015508678 | A | 3/2015 |
| WO | 2010149393 | A1 | 12/2010 |
| WO | 2012007139 | A1 | 1/2012 |
| WO | 2013082053 | A1 | 6/2013 |
| WO | 2013093001 | A2 | 6/2013 |
| WO | 20130082053 | A1 | 6/2013 |
| WO | 20130093001 | | 6/2013 |
| WO | 2013119752 | A2 | 8/2013 |
| WO | 2013120957 | A1 | 8/2013 |

OTHER PUBLICATIONS

Office Action issued in corresponding European Patent Application No. 21161641.2 dated Mar. 6, 2023, (10 pp.).

Office Acton from corresponding Korean Patent Application No. 10-2021-7035894 dated Feb. 16, 2022 (8 pp.).

Office Action from corresponding Canadian Application No. 2,925,194 dated Sep. 2, 2021 (4 pages).

International Search Report and Written Opinion for International Application No. PCT/EP2014/071705 dated Dec. 15, 2014 with English Translation (23 pages).

Office Action from corresponding Japanese Patent Application No. 2019-128877 dated Oct. 5, 2020 (21 pages).

Office Acton from corresponding Japanese Patent Application No. 2021-030621 dated Mar. 8, 2021 (9 pages).

Office Action from corresponding Chinese Patent Application No. 202110188802.X dated Jun. 21, 2023 (22 pp.).

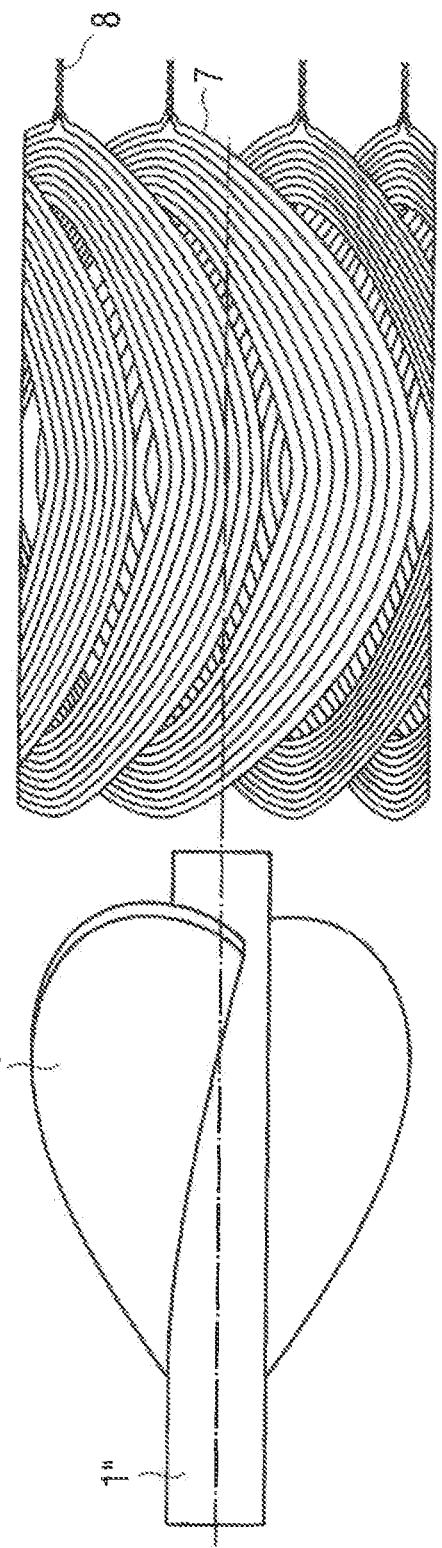

COMPRESSIBLE MOTOR, IMPLANTATION ARRANGEMENT, AND METHOD FOR POSITIONING THE MOTOR

CROSS-REFERENCE TO RELATED APPLICATIONS

The present application is a continuation of U.S. patent application Ser. No. 16/436,000, filed Jun. 10, 2019, now allowed, which is a continuation of U.S. patent application Ser. No. 15/662,884, filed Jul. 28, 2017, now U.S. Pat. No. 10,342,904, which is a continuation of U.S. patent application Ser. No. 15/028,588, filed Apr. 11, 2016, now U.S. Pat. No. 9,750,860, which is a national phase entry under 35 U.S.C. § 371 of International Application No. PCT/EP2014/071705, filed Oct. 9, 2014, published as International Publication No. WO 2015/052303 A1, which claims priority to European Patent Application No. 13188380.3, filed Oct. 11, 2013, the disclosures of which are hereby incorporated herein by reference.

BACKGROUND OF THE INVENTION

The invention lies in the field of mechanics and electrical engineering and can be used particularly advantageously in the field of micromechanics. Inter alia, applications in medical engineering are particularly advantageous.

BRIEF SUMMARY OF THE INVENTION

When introducing assemblies into channel systems or at locations which are particularly difficult to access, problems often occur, similarly to when implanting assemblies into a patient body, due to the fact that assemblies of this type must be brought to their target positions through through-openings or channels that are as narrow as possible, but once arrived at the target position are to provide the greatest possible effect, inter alia by maximal dimensions.

In medical engineering, it is known for this purpose to adopt an approach in which corresponding assemblies are compressed before being introduced into the patient body and to the target location, are inserted in the compressed state, and are then expanded. This has previously already been applied in the case of expandable heart-assist catheter pumps and also in the case of implantable stents. In the non-medical field, inspection cradles by way of example can be sent through tubes and can likewise be expanded once they have reached larger cavities or can be used to deploy suitable tools or sensors.

In the medical field drivable, expandable assemblies were until now driven, when implanted, by motors outside the body by means of flexible shafts. In the case of heart-assist blood pumps, a pump rotor for example is connected to a motor outside the body by a port by means of a flexible shaft, which extends through a hollow catheter within blood vessels. Very high demands are sometimes placed on transfer systems of this type, for example in the form of flexible shafts, since these high rotational speeds must be transferred over a relatively long period of time without significant wear and usually under lubrication conditions which are not optimal. It would therefore be advantageous to be able to dispense with transfer systems of this type.

Against the background of the prior art, the object of the present invention is therefore to design a motor in such a way that it can also be transported through narrow channels. The object is achieved by the features described herein.

The motor according to the invention has a stator and a rotor that can be driven about an axial direction, wherein, in order to achieve the object, of these, at least one, in particular the stator, which has a winding arrangement that can be supplied with a current, is radially compressible and expandable.

The term radial compressibility within the scope of the present invention is to be understood to mean that the diameter of the element in question can be reduced at least in part in relation to the axis of rotation of the motor. This may include all possibilities of a uniform diameter reduction, in which case merely the diameter of a cylindrical body changes, without otherwise changing in terms of shape. However, the radial compressibility may also be understood to mean diameter reductions of the stator and/or the rotor in just one axis, which for example is generated by pressing the element flat or, if the element (stator and/or rotor) is composed of different circular discs, by tilting the circular discs relative to the axis of rotation. In the specified case the diameter is reduced in a first direction perpendicular to the axis of rotation, whereas it remains constant in the direction perpendicular to the first direction.

Compressible stators of this type having a winding arrangement that can be supplied with a current are not known from the prior art. In accordance with the invention, the winding arrangement itself in particular may be radially compressible. A winding arrangement of this type can be compressed before being introduced into a channel, whereby the overall diameter of the motor is reduced particularly when the stator determines the outer diameter of the motor. By way of example, the stator may surround the rotor coaxially in the operating state. In this case, a radial compression of the stator is equivalent to a radial compression of the motor. The stator may also be surrounded by a housing, which for example may be resilient and then compressible and expandable with the stator. By way of example, the housing may consist substantially of a resilient film, which is stretched over the stator. However, it may also be that the motor does not have a housing.

When the stator surrounds the rotor coaxially, the possibilities for compression of the stator are subject to narrow limits by the internally arranged rotor. A further compression of the stator is advantageously possible for example when the rotor and stator can be displaced relative to one another in the axial direction between a first position, in which the stator is radially compressible, and a second position, in which the stator is radially expanded. In this case, for compression of the stator, the rotor can be firstly slid out therefrom axially, and the stator can then be compressed, for example up to the outer diameter of the rotor. The stator and rotor can then be slid axially one after the other through a channel to the target position. If the rotor per se is not compressible, a further compression of the stator under the external dimension of the rotor therefore is not provided or is not possible in some exemplary embodiments.

If the stator and rotor have arrived at the target position, the stator can be expanded again or can expand automatically, and the rotor can be drawn into the stator in the axial direction.

The stator may also be radially expanded in that the rotor is displaced or drawn into the stator and this is radially expanded during the displacement movement. For this purpose, the rotor may be formed in a conically tapering manner at least in portions.

In accordance with a further advantageous variant of the invention, the rotor is compressible in the radial direction. If the rotor is also compressible in the radial direction, the rotor in a variant may remain in the stator, and both can be radially compressed jointly, otherwise it is also conceivable to displace the rotor out from the stator and to compress these both radially independently of one another.

By way of example, the rotor for this purpose may have a plurality of magnets, which can be referred to as magnet elements and which are reversibly movable relative to one another in particular in the axial direction. The rotor by way of example may have permanent magnets or electromagnets having a ferromagnetic core, which are each to be designated as magnet elements. Such magnets can each be divided into magnet segments in such a way that individual segments of a magnet can be displaced relative to one another in order to reduce the diameter of the rotor by reduction of the dimensions of the magnets in the radial direction.

By way of example, at least one magnet may consist of wedge-shaped segments, which can be pushed together and away from one another in the axial direction and when pushed away from one another take up less space on the whole, as considered in the radial direction, than when in the state pushed together. However, a division in different other planes may also be provided, wherein it is also conceivable to displace the individual segments of the magnet in the circumferential direction of the rotor and/or in the radial direction of the motor. The segments of the magnet may also be referred to as magnet elements, and therefore the term magnet elements includes both the segments of the magnet and entire magnets.

It is important that the described movements of the magnets or the segments of magnets lead to a diameter reduction, are reversible, and can be reversed in a simple manner for a subsequent expansion of the rotor.

In order to enable the simplest possible radial compression of a stator, the winding arrangement advantageously may have at least one sub-winding for example, which is reversibly deformable. By way of example, sub-windings of this type may be resilient and for example may contain resilient leads, which allow a temporarily deformation of a sub-winding. A deformation of this type may be both resilient and plastic.

It may also be that the winding arrangement has at least two sub-windings, which can be displaced reversibly relative to one another. Sub-windings of this type for example may be non-cast or may be cast in a rigid or resilient casting material and may be slid one over the other in a shingle-like manner, in particular in the circumferential direction of the stator, in the event of radial compression of the stator. However, a pivoting or rotation of sub-windings is also conceivable, provided the rotor has been removed from the stator.

For improved deformability of the winding arrangement, the winding arrangement for example may have at least one sub-winding cast in a resilient material. By way of example, a sub-winding may be cast in an elastomer, for example in a silicone elastomer or in a rubber material. Larger parts of the winding arrangement, for example even the entire winding arrangement, may also be cast in a resilient material of this type.

In order to increase the efficacy, the resilient matrix may be provided in particular on the outer side with a ferromagnetic filler.

If individual parts of the winding arrangement are each cast separately, the resilient deformability can thus also be combined with a displaceability, for example when the sub-windings have resilient leads and/or are cast in a resilient material.

By way of example, the winding arrangement may also have, at least in part, leads consisting of a memory alloy. In this case, a sub-winding or the entire winding arrangement may assume a desired shape and size at the target location, for example by selective setting of a target temperature. In the case of medical applications, the alloy for example may be set such that the winding arrangement assumes the desired target shape once the body temperature of a patient has been assumed.

In order to ensure a repeated compression and expansion and a reproducible course of the compression and expansion movement in the case of a winding arrangement consisting of a plurality of sub-windings movable relative to one another, it may also be advantageous for example for the winding arrangement to have bend and/or kink regions defined between elements movable relative to one another. Bend and/or kink regions of this type may be provided in the form of soft and/or flexible lead parts, for example by providing length portions of the leads formed as stranded wires or by particularly thin lead regions.

In the case of a motor of the above-described type, in order to be able to displace the rotor and stator relative to one another in the target position, even from a distance, the invention advantageously provides a connection element, which extends away from the motor and by means of which the rotor and stator can be displaced relative to one another in the axial direction. The connection element can be formed as a typical manipulation element, for example in the manner of a Bowden cable or the like, wherein different parts of the connection element can be connected to the stator on the one hand and the rotor on the other hand.

By means of the connection element, a relative displacement of the stator and rotor and therefore in the target position a drawing of the rotor into the stator is possible, wherein the stator either has been already expanded beforehand or is radially expanded by drawing the rotor into the stator.

The invention also relates to an implantation arrangement having a hollow catheter and a stator and a rotor arranged compressed therein. Within the scope of an implantation arrangement of this type, the radially compressible motor can be drawn in simple form into a hollow catheter, wherein the motor is usually received in the hollow catheter in the compressed form. The hollow catheter may then for example be introduced by means of a port into a blood vessel of a patient, displaced through this, and taken to a target position, for example introduced into an aortic arch, into a cardiac valve or into a ventricle. The hollow catheter may then be retracted, wherein the motor is slid out therefrom and is either radially expanded during this process or thereafter.

The invention also relates to a motor of the above-described type and to an implantation arrangement, and to a method for positioning a motor of the described type, wherein the stator and the rotor are displaced through a channel to a target position, wherein at least the stator is radially compressed, and at least the stator is radially expanded thereafter.

In accordance with an advantageous embodiment of the method the stator and the rotor are displaced relative to one another in the axial direction once the stator and rotor have been displaced into the target position.

The invention also relates to a pump, in particular blood pump, containing a motor having a stator and a rotor that can be driven about the axial direction, wherein, of these, at least one, in particular the stator, which has a winding arrangement that can be supplied with a current, is radially compressible and expandable. Here, the motor and the pump are advantageously integrated heavily in one another. It is thus possible to produce pumps of particularly small structure; in particular it is advantageous for pumps having a very small radial diameter to be brought to a site of use and then radially expanded there in order to provide the actual pump performance.

Here, in accordance with an embodiment, the rotor is connected to a pump rotor, wherein the pump rotor has a blading for conveying fluids. By way of example, the pump rotor can be mounted on the actual magnetic rotor or may surround this radially; it is also possible however for these to be interconnected in another way, for example in that the magnetic rotor is cast/embedded in the pump rotor.

In accordance with a further embodiment the pump rotor in the operating state is located at least partially within the stator. A radial layered arrangement is thus provided in the operating state and, starting radially outwardly towards the center, is as follows: 1. stator, 2. pump rotor, 3. magnetic rotor. In other forms in which the pump rotor and the magnetic motor are interconnected, this potentially may also be different.

In accordance with an advantageous embodiment, the pump rotor is radially compressible, in particular the pump rotor is radially resiliently compressible. Here, in accordance with a variant, the blading of the pump rotor is primarily resiliently compressible and for example bears against the hub of the pump rotor.

Different variants of the pump according to the invention are possible, wherein all variants of the motors according to the present invention can be used for the pump.

BRIEF DESCRIPTION OF THE DRAWINGS

The invention will be shown in various figures and described hereinafter on the basis of exemplary embodiments. In the figures FIG. 20 shows an illustration of a stator having a pump rotor removed therefrom axially, in a side view.

DETAILED DESCRIPTION OF THE DRAWINGS

Figure 1:
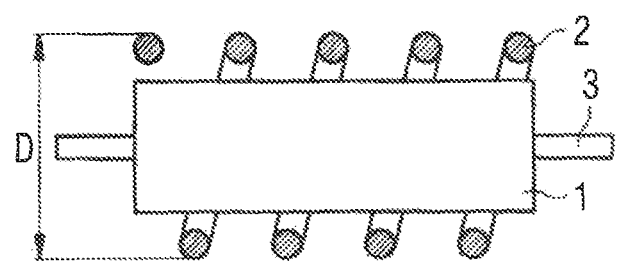
FIG. 1 shows a schematic illustration of a motor having a rotor and a stator in a longitudinal section.

FIG. 1 schematically illustrates, in a longitudinal section, a stator 2 and a rotor 1 of an electric motor. Further parts and details have been omitted for the sake of clarity. The stator has a schematically indicated cylindrical winding arrangement, which may consist of one or more sub-windings. The rotor 1 has at least one permanent magnet and a hub, which is connected to a shaft 3. The magnetic poles of the rotor 1 or of the magnet/magnets thereof can be driven in the magnetic field of the stator 2. The shaft 3 is usually rotatably mounted at one or more points in plain or ball bearings. The bearings may be fixedly connected for example to the stator 2 or to a housing (not illustrated) of the stator or the motor as a whole. In FIG. 1 it can be seen that the stator, which surrounds the rotor 1 concentrically and coaxially, has a diameter D in the radially expanded state illustrated there.

Figure 2:
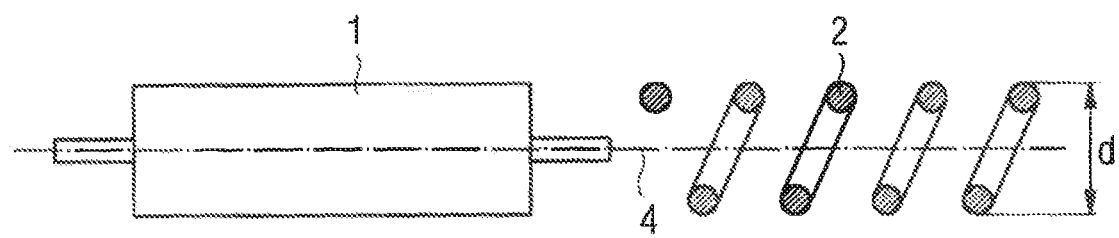
FIG. 2 shows the motor from FIG. 1 in a compressed form, wherein the stator and rotor are pulled axially away from one another, FIG. 3 schematically shows, in a modified form, individual wires of the winding arrangement with a length reserve in the form of a spiraled or meandering course.

FIG. 2 shows the elements of a motor already illustrated in FIG. 1, specifically a rotor 1 and a winding arrangement of a stator 2, wherein the rotor and stator are pulled apart from one another in the axial direction 4. The stator and the rotor do not overlap one another in the axial direction in this state. The stator is radially compressed by radial compression of the winding arrangement on the whole to the diameter d, which is equal to or smaller than the outer diameter of the rotor 1.

Is thus clear that, due to the divisibility of the motor and the displaceability of the stator relative to the rotor, the stator is radially compressible as soon as the rotor has been removed therefrom.

Irrespective of this and in addition, the rotor may also be compressible in the radial direction. In this case, the stator and rotor may also be radially compressed jointly in the assembled state, or can be displaced axially relative to one another and can both be radially compressed separately from one another. In the latter case it is useful, but not necessary, for both elements, i.e., both the stator and the rotor, to be compressible approximately to the same outer diameter.

Figure 3:
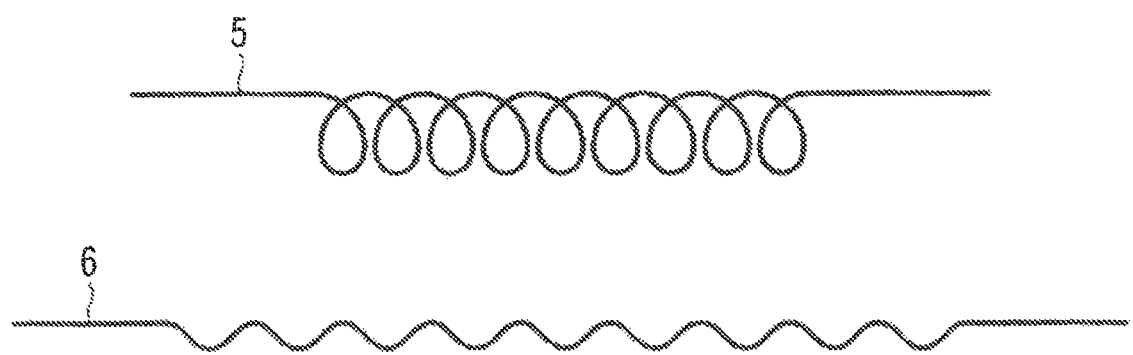

FIG. 3 in the upper region shows a first lead 5 of a winding arrangement of a motor according to the invention in the compressed state, wherein the lead extends in a spiraled manner. If a winding arrangement or sub-winding is formed from this lead extending in a spiraled manner, this winding arrangement or sub-winding can radially expand if the winding wire 5 is extended and later can be radially compressed again. In the lower region of FIG. 3 a lead 6 is illustrated, which in the compressed state has a meandering form which can be extended when transitioning into an expanded state.

Figure 4A:
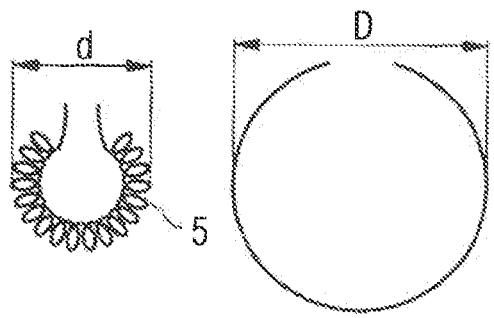
FIG. 4a shows an illustration of a winding arrangement in an axial view, compressed in the left-hand part of the figure in the spiraled form of the lead, and expanded on the right-hand side.

In FIG. 4a a lead 5 that is spiraled in the compressed state is illustrated schematically in the left-hand part and likewise in the compressed state is illustrated schematically in the form of a circular ring, which symbolizes a winding arrangement. In the right-hand part of FIG. 4a, an expanded form of the stator is illustrated in axial view, in which the winding lead(s) is/are elongated and accordingly the winding arrangement and/or the sub-windings is/are likewise expanded. The stator in the right-hand part of FIG. 4a has the enlarged diameter D, whereas in the compressed state illustrated in the left-hand part of FIG. 4a it has the reduced diameter d.

Figure 4B:
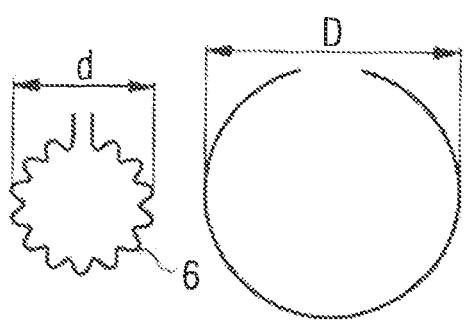
FIG. 4b shows a winding arrangement as considered in the axial direction, compressed in the left-hand part of the figure in the meandering form of the lead, and radially expanded in the right-hand part.

In FIG. 4b a compressed lead 6 is illustrated in meandering form, which, as considered in the axial direction, is arranged in a circular ring form, which represents a winding arrangement of a stator. The arrangement has the compressed outer diameter d. In the right-hand part of FIG. 4b the same stator is illustrated in the radially expanded state, wherein the winding lead(s) is/are elongated, or at least are further extended than in the compressed state.

The transition between the compressed and expanded state of the stator can be implemented for example by an application of force, in that the stator is brought by means of radial external pressure into a compressed form and, when the external radial compression force is cancelled, expands resiliently again of its own accord.

Conversely, the stator may also have a reduced diameter without external force application, and may be expandable by force application.

As a further alternative, it may be that the winding arrangement has leads made of what are known as memory alloys, which for example in the event of temperature changes change their shape and in defined temperature ranges each have reproducible shapes. Such memory alloys may be, for example, NiTi (nickel-titanium; nitinol), NiTiCu (nickel-titanium-copper), CuZn (copper-zinc), CuZnAl (copper-zinc-aluminium), CuAlNi (copper-aluminium-nickel), FeNiAl (iron-nickel-aluminium), or FeMnSi (iron-manganese-silicon). Alloys of this type are also referred to as hyperelastic alloys.

In addition to the described properties of the winding arrangement, a casting of the entire winding arrangement or individual sub-windings in a resilient material, such as a silicone elastomer or a rubber, may also be provided, which is resiliently deformable per se. There may also be no casting of the winding arrangement, or a casting in a non-resilient material, wherein the casting of individual sub-windings is performed separately and the sub-windings together with the respective casting material are movable relative to one another. Such configurations will be discussed in greater detail further below.

Figure 5:
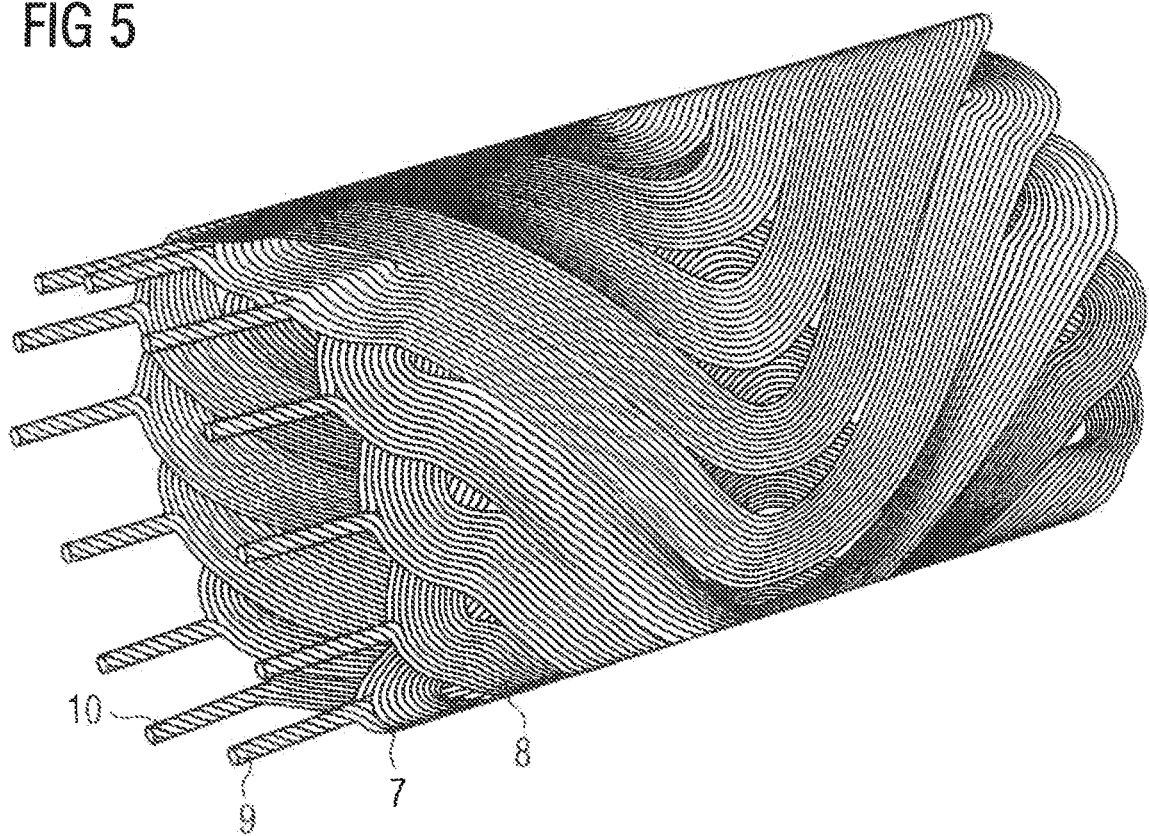
FIG. 5 shows, in a three-dimensional view, a winding arrangement having a plurality of sub-windings, which in the unrolled state have substantially a rhombic or trapezoidal design, FIG. 6 schematically shows, in a three-dimensional view, the course of an individual winding of a sub-winding from FIG. 5, FIG. 7 schematically shows, in a view in the axial direction, the arrangement of different sub-windings relative to one another at the circumference of the winding arrangement in the radially expanded state.

FIG. 5, in a perspective view, shows a substantially hollow-cylindrical winding arrangement, which consists of a plurality of sub-windings. Each sub-winding consists of a plurality of windings of a lead and has two electrical terminals for voltage supply and current feed. The winding arrangement as a whole may also have terminal leads or electrical terminals.

Each sub-winding of the illustrated winding arrangement in the unrolled state has a rhombic basic shape. The individual sub-windings overlap one another in the circumferential direction of the winding arrangement. The individual sub-windings 7, 8 of the winding arrangement from FIG. 5 have electrical terminals 9, 10 for supplying a current to the stator winding arrangement.

Figure 6:
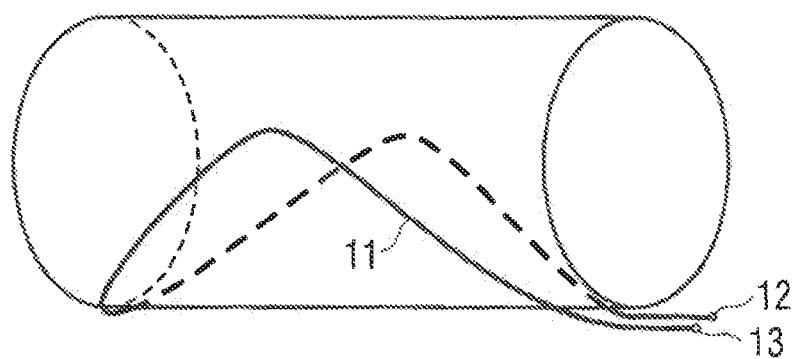

In FIG. 6 an individual sub-winding 7 is illustrated, symbolized by an individual winding of a winding lead, and is designated by reference sign 11. The sub-winding 11 has two electrical connections 12, 13 for supplying a current. In FIG. 6 a hollow cylinder is illustrated schematically, over the circumference of which the part-cylindrical sub-windings are distributed in a manner overlapping one another and offset relative to one another in the circumferential direction.

Figure 7:
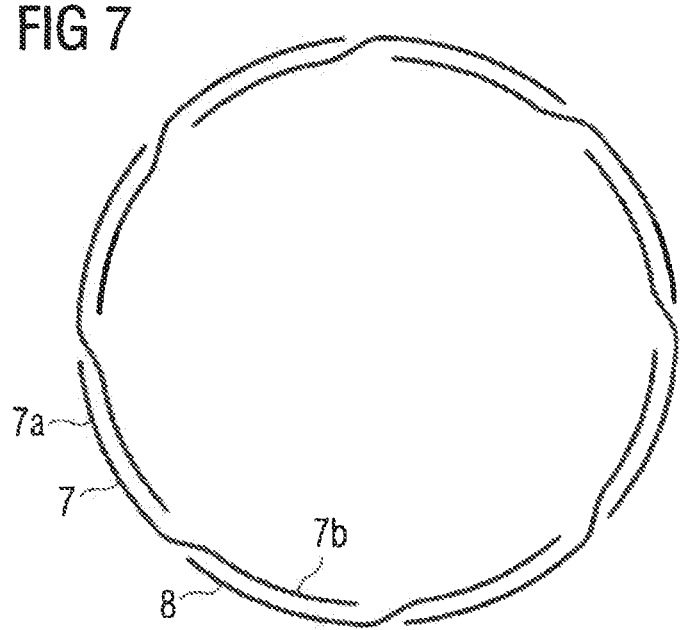

In FIG. 7 a plurality of sub-windings 7, 8 of a winding arrangement are shown schematically in a view in the axial direction. The individual sub-windings 7, 8 each have a radially external part 7a and a radially inner part 7b, wherein each radially inner part is overlaid by the following sub-winding 8, more specifically by the radially external part thereof. In this way, a roof-tile-like nesting of the sub-windings is provided along the circumferential line of the stator.

Figure 8:
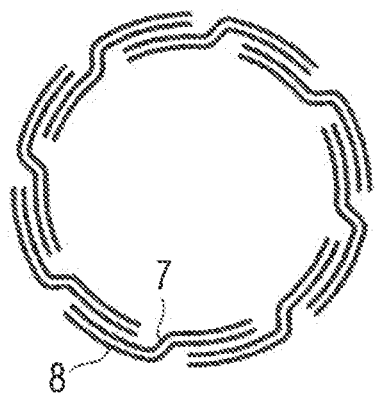
FIG. 8 shows the arrangement of sub-windings from FIG. 7 in the radially compressed state, FIG. 9 schematically shows a longitudinal section through a motor having a stator and a rotor, wherein the rotor is encapsulated, in the assembled, expanded state.

If the sub-windings are movable relative to one another, these can be slid further over one another in a shingle-like manner, and therefore the diameter of the overall arrangement and the circumference of the winding arrangement can be reduced. An example of a compressed state of such a compression movement is shown in FIG. 8, in which in each case two windings 7, 8 are slid one over the other, such that they overlap one another completely in the circumferential direction of the winding arrangement. This slidability of the individual sub-windings over one another is conceivable with non-cast sub-windings and also with cast sub-windings. If the individual sub-windings are cast, it is advantageous if the casting material enables easy sliding relative to one another of two bodies consisting thereof.

Figure 9:
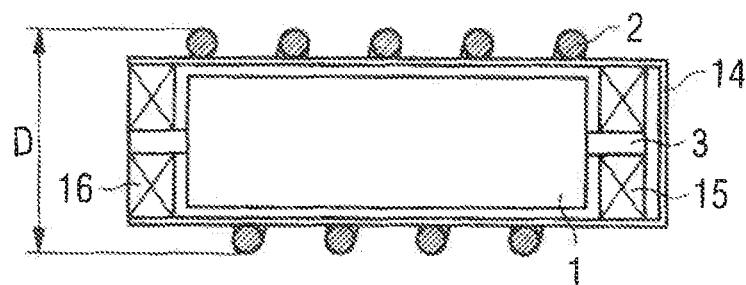

FIG. 9, in a longitudinal section, shows a motor having a radially expanded stator 2 and a rotor 1, which has an encapsulation 14 in the form of a hollow cylinder, which surrounds the magnet body of the rotor and which for example also carries the bearings 15, 16. The shaft 3 of the rotor is mounted with little friction in the bearings 15, 16, which may be formed as plain or ball bearings. The diameter of the overall structure of the motor according to FIG. 9 in the expanded, assembled state ready for operation is specified by D.

Figure 10:
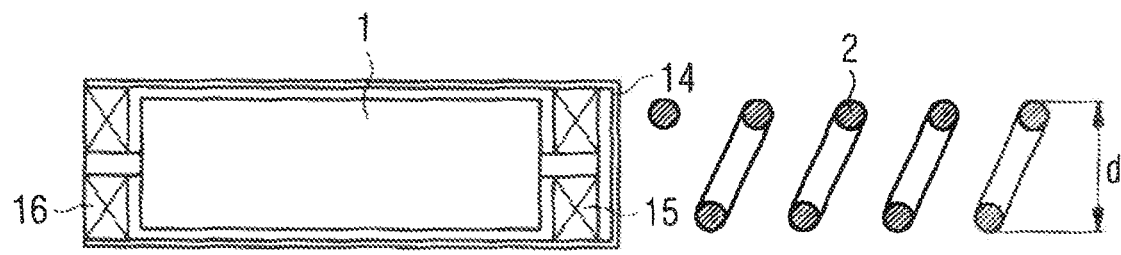
FIG. 10 shows the motor from FIG. 9 in the compressed state pulled apart axially.

By contrast, the same motor having the same elements, i.e., a rotor encapsulated within an encapsulation 14 and a stator 2 having a winding arrangement, is illustrated in FIG. 10 in the compressed state, wherein the stator 2 has been displaced to such an extent in the axial direction relative to the rotor 1 that the rotor is located outside the stator. The stator 2 is then radially compressible independently of the rotor 1 up to the outer diameter of the rotor.

Figure 11:
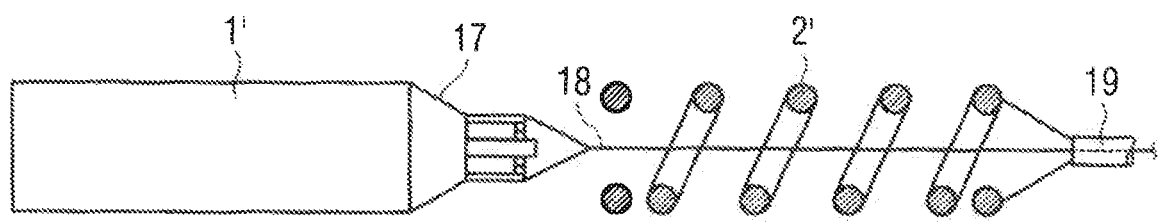
FIG. 11 shows a stator and a rotor arranged axially in succession, wherein the stator is radially compressed and both have a manipulation means.

FIG. 11 shows a design of a motor having a rotor 1' and a stator 2', wherein these are illustrated in the compressed position pulled apart axially from one another. The rotor 1' has an encapsulation, in which the magnet arrangement of the rotor, supported by two bearings, can rotate. The encapsulation of the rotor has a conical tapered portion 17 and a connection to a strand-shaped manipulation element 18, which is fastened to the encapsulation or to a bearing and enables an axial relative movement of the rotor relative to the stator 2'. At the same time, the stator 2' is connected to a second manipulation element 19, for example in the form of a tube or hose, through which for example the manipulation element 18 can be guided. The manipulation elements 18, 19, which jointly form a connection element to the motor, can be jointly actuated from a remote location in order to perform a relative movement of the stator and rotor relative to one another and for example to radially expand these by means of the insertion of the encapsulation of the rotor 1' into the winding arrangement of the stator 2'.

Figure 12:
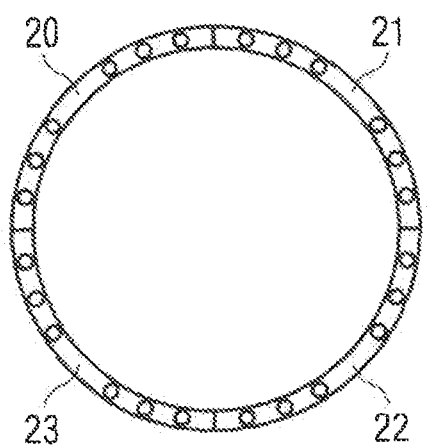
FIG. 12 shows a cross section through a stator, of which the winding arrangement is divided in the circumferential direction into four sub-windings.

FIG. 12 shows a particular winding arrangement consisting of four separate sub-windings 20, 21, 22, 23 each cast separately in a resilient material. Each of these sub-windings is formed as part of a hollow cylinder, and the sub-windings can be assembled with their cast bodies to form an overall hollow cylinder.

Figure 13:
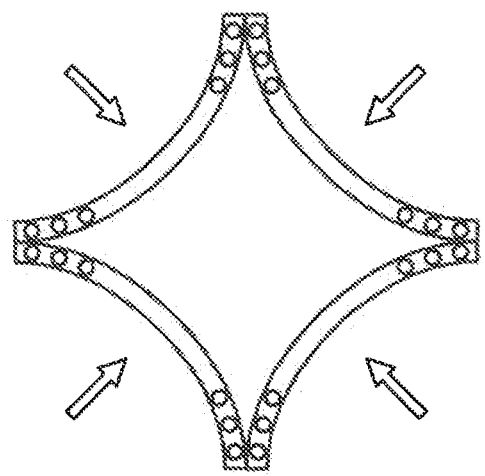
FIG. 13 shows a compressed state of the stator from FIG. 12, in which the sub-windings have been changed mechanically radially inwardly by radial pressure.
Figure 14:
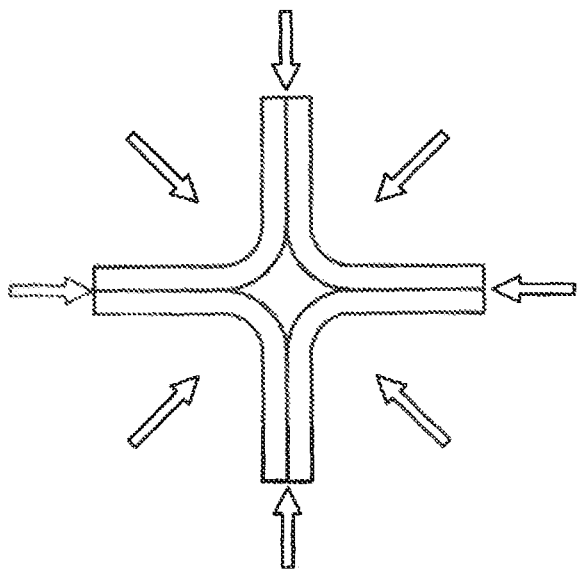
FIG. 14 shows an illustration of the stator from FIGS. 12 and 13 in the further compressed state, FIG. 15 schematically shows, in the axial direction, the illustration of a rotor having two magnets.
Figure 15:
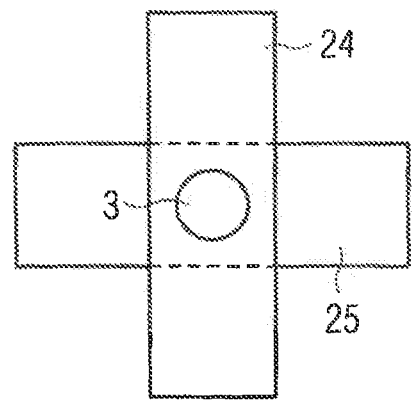

If a force is exerted onto the winding arrangement radially from the outside, the constellation as illustrated in FIG. 13 is provided, wherein the individual cast bodies and sub-windings turn radially inwardly. The individual cast bodies of the sub-windings may be connected movably to one another for example by living hinges. In the state illustrated in FIG. 13, the winding arrangement in the radial direction already occupies a much smaller space than in the form illustrated in FIG. 12. With a further radial compression, the individual sub-windings are further compressed radially inwardly, which is additionally made possible by a deformability of the cast body. With full compression, the form illustrated in FIG. 14 is provided. This can be automatically expandable back into the form illustrated in FIG. 12 with cancellation of the radially inwardly acting compression forces, wherein the restoring forces can be applied for example by the resiliently deformed cast bodies, but also by the winding leads themselves, or by both, jointly. If the individual sub-windings are not cast, a corresponding deformation of the winding leads can also take place reversibly within each sub-winding. FIG. 15, in an illustration in the axial direction, shows two magnets 24, 25 arranged at right angles on one another, which can be driven in the magnetic field of the winding arrangement. The magnets 24, 25 are fixedly connected to the shaft 3 of the rotor.

Figure 16:
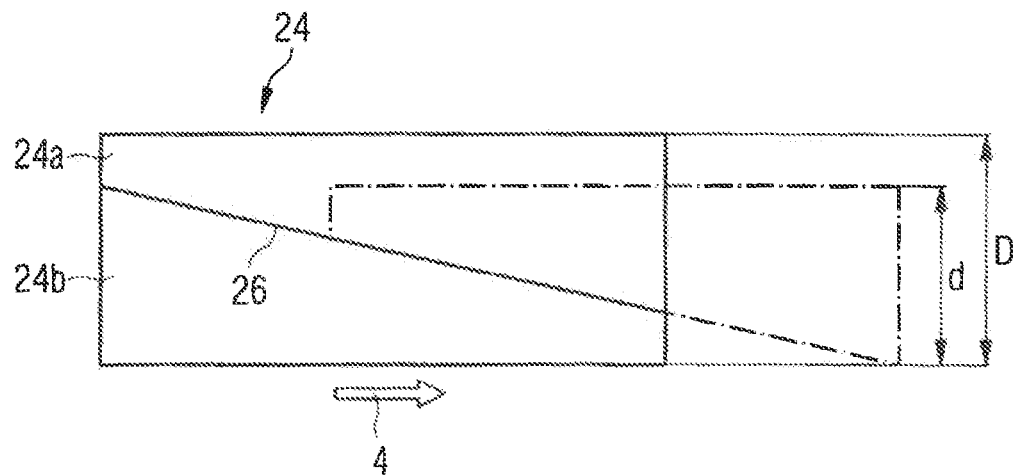
FIG. 16 shows a side view of a magnet of a rotor divided into segments and radially compressible.

FIG. 16 illustrates the division of a magnet 24 along the surface 26, whereby two segments 24a, 24b of the magnet 24 are produced, which each form a magnet element. The magnet 24 in the state illustrated by solid lines, has the form of a cuboid. The constellation in which the segment 24 is displaced in the axial direction 4 along the surface 26 relative to the segment 24b is shown in a dashed manner. An extension of the magnet 24 is provided in the axial direction, and a compression from the diameter D to the diameter d, as specified in FIG. 16 in the right-hand part, is provided in a radial direction. As a result of the shown construction of the rotor, this can also be radially compressible, such that the motor is compressible either in the assembled state by joint compression of stator and rotor or is also compressible merely by radial compression of the stator in the state pulled apart axially.

The motor can therefore be compressed in order to be brought to its site of use; for example, it may be implantable as a drive apparatus for a blood pump and may be displaced through a blood vessel in the compressed state within a patient body to a site of use. There, the motor can be expanded, as can a blood pump for example, and the motor in the expanded state can build up the necessary torques or the required power to drive a pump.

Figure 17:
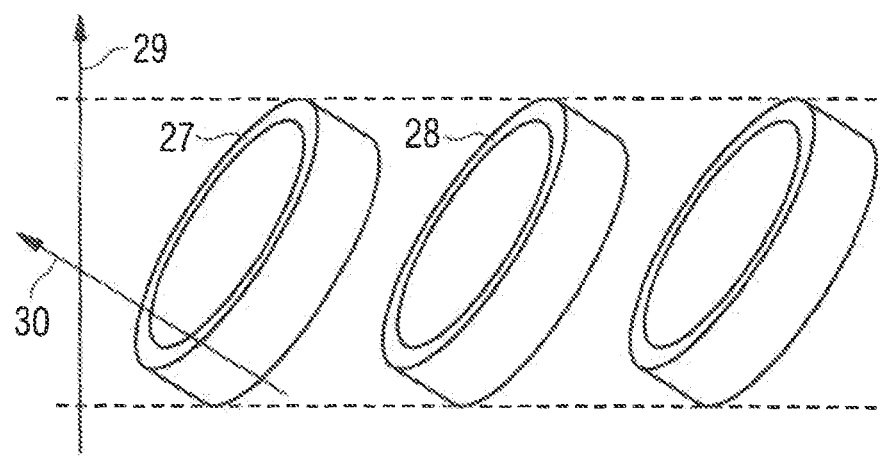
FIG. 17 shows an illustration of a stator having a winding arrangement divisible in the axial direction.

FIG. 17 shows a design variant in which the winding arrangement is divided into a plurality of sub-windings 27, 28, which are each constructed in the form of a circular ring and, arranged axially in succession, form a hollow-cylindrical winding arrangement. If, in such an arrangement, the circular-annular sub-windings are tilted, the cross section of the winding means is thus elliptical, but is compressed in diameter in an axis 29 relative to the untilted arrangement. In the axis 30 arranged at right angles hereto, the diameter remains the same. Nevertheless, a form more favorable for the positioning of the motor may be provided with the tilted arrangement. The tilting can be reversed at any moment following the positioning of the motor.

Figure 18:
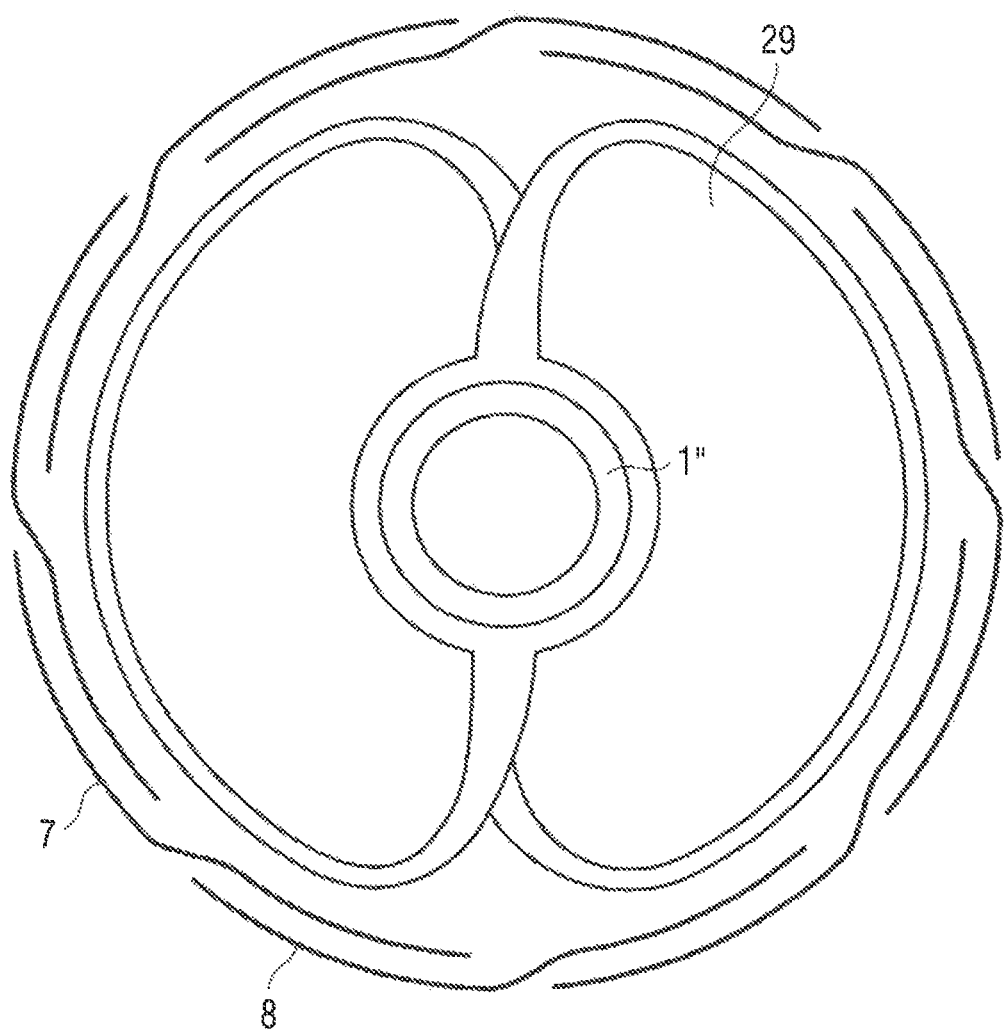
FIG. 18 shows an illustration of a stator having a rotor arranged therein and a compressible pump rotor arranged on the rotor in the expanded state.

FIG. 18 shows a device consisting of a stator according to FIG. 7 having the windings 7, 8 already described there. A magnetic rotor 1", to which a radially compressible pump rotor 29 is connected in such a way that it can rotate jointly with the rotor 1" about the same axis, is located in this stator. In the exemplary embodiment the pump rotor is formed from a resilient, preferably hyperelastic plastics material, which makes it possible for the pump rotor 29 to collapse in the event of compression of the stator and to resiliently or hyperelastically expand back again into the starting form in the event of expansion of the stator.

Figure 19:
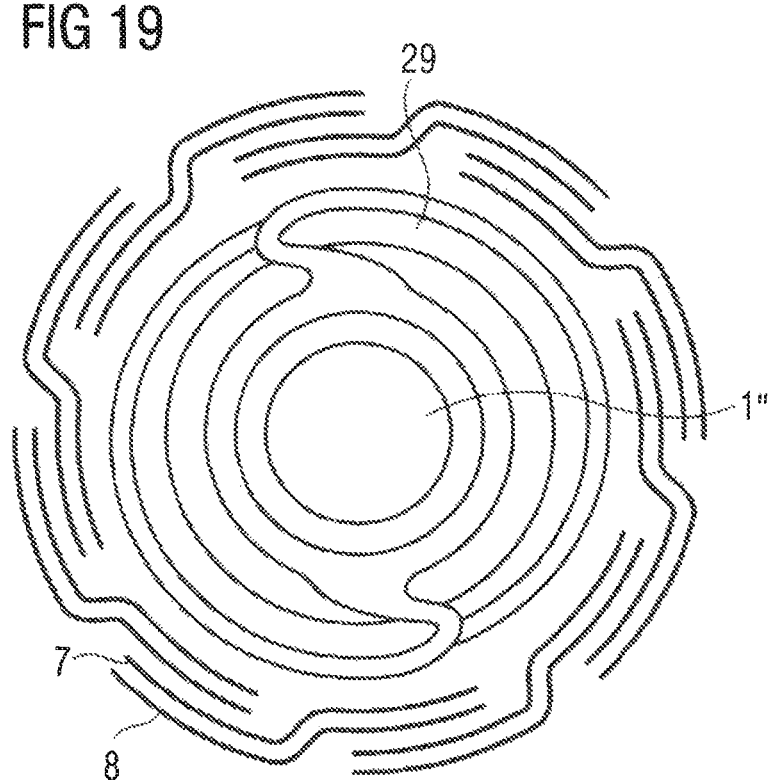
FIG. 19 shows an illustration of the device from FIG. 18 in the compressed state.

FIG. 19 schematically illustrates how the stator compresses similarly to FIG. 8, wherein the pump rotor 29 likewise assumes a compressed form. Here, the blades of the pump rotor fold around the axis of the rotor and bear against the hub of the pump rotor.

In principle, the device may also be formed such that the rotor 1" together with the pump rotor 29 can be axially removed from the rotor in a manner corresponding to FIG. 20. The pump rotor 29 and the stator are thus arranged axially in succession. In this state the stator and the pump rotor can be jointly compressed, which enables a further reduction of the compressed diameter compared with the embodiment in FIG. 19.

The pump rotor can be formed in principle in very different ways. Besides the variant formed from resilient or hyperelastic plastics material shown in FIGS. 18 and 19, various other variants are known from the prior art, for example from U.S. Pat. Nos. 4,753,221; 5,749,855; 7,393,181; US 2009/0062597 A1; EP 2047873 A1; US 2011/0275884 A1; EP 2229965 A1; WO 2010 149393 A1; EP 2299119 A1; EP 2338540 A1; EP 2338541 A1; EP 2363157; EP 2407185 A1; EP 2407187 A1; EP 2407186 A1.

The invention claimed is:

1. A motor, comprising:
a rotor that can be driven about an axial direction; and
a stator, which has a winding arrangement that can be supplied with a current;
wherein the stator is radially compressible and expandable; and wherein the winding arrangement has at least one sub-winding cast in a resilient material.

2. The motor according to claim 1, wherein the rotor and the stator can be displaced relative to one another in the axial direction between a first position, in which the stator is radially compressible, and a second position, in which the stator is radially expanded.

3. The motor according to claim 2, further comprising a connection element, which extends away from the motor and by means of which the rotor and stator are displaceable relative to one another in the axial direction.

4. The motor according to claim 1, wherein the rotor is compressible in the radial direction.

5. The motor according to claim 4, wherein the rotor has a plurality of magnet elements, which are reversibly movable relative to one another.

6. The motor according to claim 1, wherein the winding arrangement has at least two sub-windings which are cast in separate sub-bodies and are movable relative to one another.

7. The motor according to claim 1, wherein the winding arrangement has leads consisting at least partially of a memory alloy.

8. The motor according to claim 1, wherein the winding arrangement has elements movable relative to one another and bend and/or kink regions defined between said elements.

9. The motor according to claim 1, wherein the rotor is radially compressible and expandable.

10. The motor according to claim 1, wherein the at least one sub-winding is a plurality of side-windings that form a cylinder.

11. The motor according to claim 10, wherein the plurality of side-windings are connected by living hinges.

12. A method for positioning a motor, the method comprising:
inserting a stator and a rotor through a channel to a target position, wherein at least the stator is radially compressed, wherein the stator has a winding arrangement that can be supplied with a current and that has at least one sub-winding cast in a resilient material; and
radially expanding at least the stator such that the at least one sub-winding cast in a resilient material also expands, thereafter.

13. The method according to claim 12, further comprising:
after inserting the stator and the rotor through a channel into the target position, displacing the stator and the rotor relative to one another in an axial direction.

14. The method according to claim 12, wherein the at least one sub-winding is a plurality of side-windings that form a cylinder.

15. The method according to claim 14, wherein the plurality of side-windings are connected by living hinges.

16. A pump comprising:
a motor having a stator and a rotor, wherein the rotor can be driven about an axial direction, wherein the stator, which has a winding arrangement that can be supplied with a current, is radially compressible and expandable and wherein the winding arrangement has at least one sub-winding cast in a resilient material.

17. The pump according to claim 16, wherein the rotor is connected to a pump rotor, wherein the pump rotor has a blade for conveying fluids.

18. The pump according to claim 17, wherein the pump rotor in an operating state is located at least partially within the stator.

19. The pump according to claim 17, wherein the pump rotor is radially compressible.

20. The pump according to claim 17, wherein the pump rotor is radially resiliently compressible.

21. The pump according to claim 16, wherein the rotor is radially compressible and expandable.

22. The pump of claim 16, wherein the at least one sub-winding is a plurality of side-windings that form a cylinder.

23. The pump of claim 22, wherein the plurality of side-windings are connected by living hinges.

* * * * *